United States Patent [19]

Celli

[11] 4,308,179

[45] Dec. 29, 1981

[54] PERFUMED COMPOSITIONS

[75] Inventor: Charles Celli, Eaubonne, France

[73] Assignee: Societe Anonyme Roure Bertrand Dupont, Paris, France

[21] Appl. No.: 785,568

[22] Filed: Apr. 7, 1977

Related U.S. Application Data

[63] Continuation-in-part of Ser. No. 283,078, Aug. 23, 1972, abandoned.

[30] Foreign Application Priority Data

Sep. 1, 1971 [FR] France .................. 71 31578

[51] Int. Cl.³ .................... A61K 7/46; C11B 9/00
[52] U.S. Cl. .................... 252/522 R; 568/379
[58] Field of Search .................... 252/522; 260/586 R; 568/379

[56] References Cited

PUBLICATIONS

Leufaut, Bull. Soc. Chim. France, 1963 (6) 1210–1213.
Bedoukian, Amer. Perf. Cos. vol. 79, pp. 27–37, Apr. 1964.
Bedoukian, Perf. & Flavor Synth., Elsevier Pub., N.Y., 1967, pp. 220–225.

*Primary Examiner*—John F. Niebling
*Attorney, Agent, or Firm*—Sidney Wallenstein

[57] ABSTRACT

Perfumed compositions which may, and in most cases especially do, contain one or more odorant perfume ingredients in conjunction with up to 20%, by weight of said perfumed compositions, of the compound 2-n-pentyl-3-(2-oxopropyl)-1-cyclopentanone which is free from garlicky odors and which has a magnolia or magnolia-like odor, and which possesses the property of imparting a magnolia odor to such perfumed and odorant compositions.

9 Claims, No Drawings

PERFUMED COMPOSITIONS

This application is a continuation-in-part of application Ser. No. 283,078, filed Aug. 23, 1972, abandoned.

BACKGROUND AND PRIOR ART

In the preparation of perfumed and odorant compositions, exemplified by perfumes and other perfumed compositions such as soaps and detergent compositions, cosmetics of various kinds such as creams, lotions, etc., it has long been known to utilize various alkyl cyclopentenones, alkyl cyclopentenone derivatives, alkyl cyclopentanones or alkyl cyclopentanone derivatives to impart certain fatty-floral odors to such perfumed and odorant compositions. Such alkyl cyclopentenones and alkyl cyclopentenone derivatives or the corresponding cyclopentanones are known to art and are associated by those skilled in the art with jasmin or jasmin-like odors and have been and are used for imparting jasmin or jasmin-like odors to perfumes and other perfumed or odorant compositions in which said alkyl cyclopentenones and alkyl cyclopentenone derivatives are incorporated. Illustrative of such alkyl cyclopentanones and derivatives thereof are methyl jasmonate and methyl hydrojasmonate (or methyl dihydrojasmonate) which possess strong jasmin odors. Methyl jasmonate, for instance, has been found to be an important odoriferous constituent of Jasmin oil and, in addition to being found to be present in Jasmin oil, its structure has been established and it, as well as numbers of other alkyl cyclopentenones and derivatives thereof, have been synthesized including the aforesaid methyl dihydrojasmonate; cis-Jasmone (3-methyl-2-(cis-2-penten-1-yl)-2-cyclopenten-1-one); amyl cyclopentenone (2-n-amyl-cyclopenten-2-one-1); etc. All of the aforesaid alkyl cyclopentenones, for instance, though varying somewhat in their jasmin odor, have the common property or characteristic, as noted above, of possessing a jasmin or jasmin-like odor, or imparting jasmin notes to perfumes and other odorant compositions in which said alkyl cyclopentenones or alkyl cyclopentanones are incorporated. Illustrative literature in support of the foregoing statements are such publications as Perfume and Flavor Chemicals, Vol. I, by Steffen Arctander, published by the Author, 1969, Section 108: Amyl Cyclopentanone; Section 1786: cis-Jasmone; and Section 1789: iso-Jasone; and Vol. II by the same Author, published in 1969, Section 2076: Methyl Hydrojasmonate. As noted above, alkyl cyclopentenones and alkyl cyclopentanones generally have fatty-floral odors, and, while such odors are variable, so far as is known the odors of the alkyl cyclopentenones and alkyl cyclopentanones have universally been recognized to be of distinctly jasmin character. Illustrative examples of other alkyl cyclopentenones and alkyl cyclopentanones which have been produced, to wit, those having the following formulae:

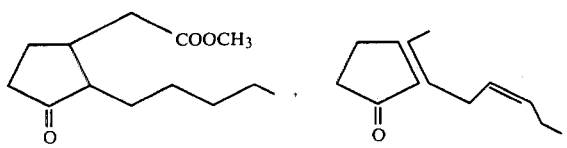

are likewise characterized by a jasmin odor.

In Bull. Soc. Chim. France, 1963(6), pp. 1210–1213, the authors, Lenfant et al, point out, with respect to methyl jasmonate, referred to above (and also referred to in Bedoukian, Amer. Perf. & Cos., Vol. 79 (1964), pp. 27–37), that it is an important ingredient or odoriferous constituent of Jasmin flower oil, and that Demole and collaborators have previously established the structure of methyl jasmonate and have effected the synthesis thereof as well as that of methyl dihydrojasmonate. Lenfant et al, in their aforesaid article, which article is also referred to in footnote 73 on p. 36 of said Bedoukian article, undertake, as an alleged interesting project, the effecting of the synthesis of certain compounds related to methyl dihydrojasmonate and to methyl jasmonate with the objective of studying the relationships which exist between structure and olfactive properties of said certain compounds. The work which they report in their aforesaid article describes the synthesis of three compounds, denoted by Roman numerals (IV), (XVIb) and (XXb), namely:

(IV). (n-amyl-2-oxo-3-cyclopentyl)-acetone, which may also be denoted as [2-(n-amyl)-3-oxocyclopentyl]-acetone.

(XVIb). methyl (n-amyl-3-oxo-4-cyclopentyl)-acetate, which also may be denoted as methyl [3-(n-amyl-4-oxocyclopentyl]-acetate.

(XXb). (n-amyl-2-carbomethoxymethyl-γ-butanolide, which also may be denoted as 2-n-amyl-carbomethoxymethyl-γ-butanolide.

Of these three compounds, compound IV, namely (n-amyl-2-oxo-3-cyclopentyl)-acetone is another chemical designation for the aforementioned compound 2-n-pentyl-3-(2-oxopropyl)-1-cyclopentanone with which the present invention is concerned.

Although, as noted above, the Lenfant et al article purports to deal with a study of the relationships which exist between structure and olfactive properties of the aforesaid compounds (IV), (XVIb) and (XXb), said article proper makes no reference whatever to the odor of compound (IV) nor, for that matter, to the odor of compounds (XVIb) and (XXb), nor to any utility or possible utility of any of said three compounds. All that is disclosed as to said compounds are the particular procedures utilized for the syntheses thereof, certain analyses of the compounds, and measurements of certain of their physical properties. Since, as noted above, alkyl cyclopentenone and cyclopentanone derivatives, in general and as exemplified by methyl jasmonate and methyl dihydrojasmonate, have long been known to possess a jasmin or jasmin-like odor, it could perhaps have been assumed or expected that the aforementioned compounds (IV), (XVIb) and (XXb) of said Lenfant et al article would, therefore, possess a jasmin or jasmin-like odor. However, as noted above, nothing whatever is stated in said article concerning any odors of said compounds nor any utility or possible utility of any of said three compounds.

In the preparation of the compound (IV) in accordance with the experimental part of said Lenfant et al article at pp. 1212–1213, a complex process is specifically described involving what amounts to a 7-stage process which may be shown in outline form as follows:

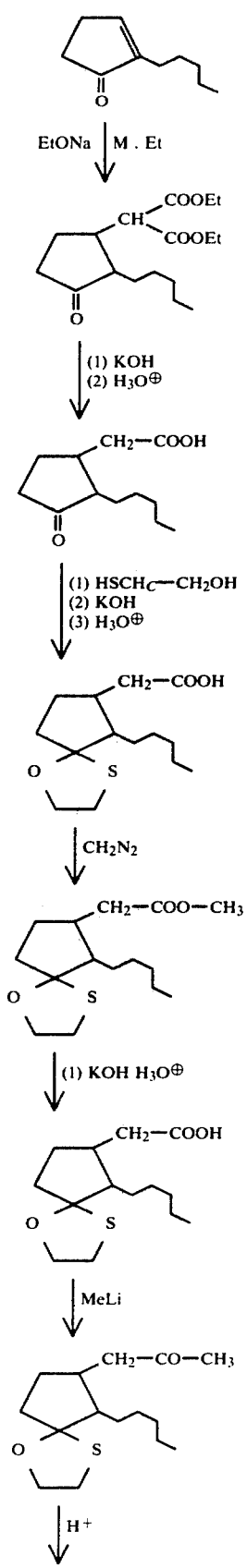

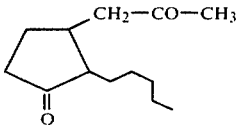

When said 7-stage process described by Lenfant et al for the production of compound (IV) is carried out, it has been found, by actual experimental work which carefully duplicated the aforesaid Lenfant et al procedure described on pp. 1212–1213 for the synthesis of compound (IV), the said compound (IV), even when separated and purified by adsorption chromatography, and fundamentally satisfying the infrared spectrum (showing two carbonyl bands) at 1736 $cm^{-1}$ (cyclopentanone) and at 1718 $cm^{-1}$ (aliphatic ketone), is not only characterized by an odor which differs substantially from the 2-n-pentyl-3-(2-oxopropyl)-1-cyclopentanone which is utilized in accordance with the process of the present invention (even at similar purity levels evidenced by essentially identical gas chromatograms as established by gas phase chromatography), but, further, the aforesaid Lenfant et al compound (IV), as prepared as described by Lenfant et al in their 7-stage process, is characterized by a garlicky odor which renders it unusable and of no value in perfumery. Hence, wholly apart from other aspects of the Lenfant et al article in relation to the invention of the present application, a matter which is discussed in further detail below, the garlicky odor of even a substantially purified compound (IV), made as specifically described by the said Lenfant et al 7-stage process, makes the compound, for all practical purposes, worthless for use as an ingredient for producing perfumed compositions. In short, while the Lenfant et al article discloses a synthesis for the preparation of what actually results, even after substantial purification treatment, in a garlicky-odor-bearing 2-n-pentyl-3-(2-oxo-propyl)-1-cyclopentanone, said article is devoid of any concept, suggestion or teaching of the present invention which involves perfumed compositions which contain a carrier which may, for instance, be a perfume, or a solid or liquid detergent, or a synthetic washing agent, or an aerosol, or a cosmetic of any kind, up to about 20%, preferably 1 to 20%, by weight of the compositions, of a 2-n-pentyl-3-(2-oxo-propyl)-1-cyclopentanone which is free from a garlicky odor, to impart a magnolia odor to the compositions, nor other features of the present invention as pointed out below.

THE PRESENT INVENTION

The present invention is directed to novel and improved perfumed compositions, which are distinguished in their containing generally up to 20% by weight, preferably from about 1 to 20%, by weight, of said compositions, as an odorant, of the compound 2-n-pentyl-3-(2-oxo-propyl)-1-cyclopentanone which compound is free from a garlicky odor and capable of imparting a magnolia odor to said perfumed compositions.

In accordance with the present invention, it has been discovered that perfumed compositions can be prepared based upon certain discoveries of novel and unexpected utilities of 2-n-pentyl-3-(2-oxopropyl)-1-cyclopentanone, when it is produced in a manner such as to be free from a garlicky odor, as, for instance, by the process described below. The novel and unknown and unexpected, and heretofore unsuspected, prior to the present invention, undisclosed utilities of garlicky-free 2-n-pentyl-3-(2-oxopropyl)-1-cyclopentanone reside in its unsuspected and surprising magnolia odor and its ability to impart a delicate and pronounced magnolia odor or fragrance to perfumed compositions, and its additional outstanding property of acting as a fixative for, and synergistically magnifying, non-magnolia floral odors in perfumes and perfumed or odorant compositions in which other odorant perfumes or perfumery ingredients and mixtures of odorant perfume or perfumery ingredients are utilized.

The source of magnolia aromas for use as odorants and perfuming agents has long, long been magnolia flower oil and magnolia leaf oil which have been extracted from fresh magnolia flowers and magnolia leaves, respectively, from magnolia trees, and other products based on extracts from magnolia flowers and magnolia leaf. However, generally speaking, such oils or extracts or the like, while to some extent available, have not been produced on any appreciable commercial scale, and relatively little is actually known of the compositions of such oils. Publications such as The Essential Oils, by Ernest Guenther, published in 1952 by D. Van Nostrand Company, Inc., New York, pp. 382 and 383; Perfume and Flavor Materials of Natural Origin, by Steffen Arctander, published by the Author in 1960 in Elizabeth, N.J., page 394; and Dott. Giovanni Fenaroli, Le Sostanze Aromatiche—Volume Primo, Sostanze Aromatiche Naturali, Editore Ulrico Hoepli Milano (1963), pp. 717-719, are illustrative of the published literature in the field dealing with magnolia perfuming or odorant materials and their disclosures are briefly summarized by what has been stated above.

The commercial production of synthetic odorants having an effective magnolia odor, and the preparation of perfumed compositions therewith, has been a significant desideratum in the perfume and odorant art for a long period of time and has not heretofore satisfactorily been met. This problem has been met and effectively solved by the present invention.

In accordance with the present invention, it has been discovered, among other things, which, as noted above, was totally surprising and unexpected, and contrary to the knowledge and teachings of the prior art, that the specific compound 2-n-pentyl-3-(2-oxo-propyl)-1-cyclopentanone, when prepared in a manner such as to be free of a garlicky odor, has a magnolia odor and can be used effectively to prepare perfumed compositions having a magnolia odor. In this connection, it is important to understand that there exists, and those skilled in the art recognize, a clear distinction between magnolia odor and jasmin odor even though these distinctly different odors generically may be characterized as floral or fatty-floral odors because magnolia oil and jasmin oil are derived from flowers, although distinctly different flowers, and in their most common or natural form, as produced from their respective flowers, are in the form of oils. Thus, for instance, in Bedoukian, Perf. & Flav. Syn., Elsevier Publ., N.Y. (1967), pp. 220-225, Bedoukian states, speaking of the alkyl cyclopentenones in general, that they have intensely powerful, fatty-floral odors valuable in jasmin and other floral compositions, but he makes no reference whatever in said statement or in connection therewith or anywhere in said article of magnolia odor, and, as has been pointed out above, prior to the present invention, the compounds within the general class of alkyl cyclopentenones have always been known, recognized and considered to have a jasmin odor or a predominately jasmin-like odor—never a magnolia or magnolia-like odor, all as has been pointed out above and as is fully supported by the literature references cited above dealing with alkyl cyclopentenone perfume materials.

With respect to the odorant or perfume properties or characteristics of the 2-n-pentyl-3-(2-oxopropyl)-1-cyclopentanone, when made so as to be free from a garlicky odor, as, for example, in the manner described hereafter, and as has been indicated above, it has been found, most surprisingly and unexpectedly, that the said garlicky-odor-free 2-n-pentyl-3-(2-oxopropyl)-1-cyclopentanone (which includes, also, its stereoisomers which, if present, can, if desired, be obtained in pure form from mixtures of said isomers by separation methods) not only does not possess a jasmin or jasmin-like odor, which jasmin odor would have been expected because of its substituted cyclopentenone structure, but, rather it possesses the property of imparting a particularly fragrant magnolia or magnolia-like odor to many perfume compositions. Thus, not only does it possess unexpectedly magnolia odor notes or a magnolia-like odor but it has additional totally surprising and important advantages, which have been indicated above, namely, of functioning effectively as fixative for other perfume or odorant materials and synergistically magnifying floral odors in perfumes and odorant compositions in which other perfume or perfumery ingredients and mixtures of perfumery ingredients are utilized. Thus, the said garlicky-odor-free 2-n-pentyl-3-(2-oxopropyl)-1-cyclopentanone is highly valuable for the preparation of perfumes as well as for the preparation of perfumed products, for example, perfumes, solid and liquid detergents, synthetic washing agents, aerosols or cosmetic products of all kinds. In perfumed compositions made in accordance with the teachings of the present invention, such perfumes, perfumed products and odorant compositions may contain from up to 20%, preferably 1 to 20%, by weight, as noted above, preferably 5 to 10%, of the garlicky-odor-free 2-n-pentyl-3-(2-oxopropyl)-1-cyclopentanone. The present invention opens an important new avenue in the perfumery and odorant art, something which was previously unknown, since extracts, oils, concrete, and the like forms of magnolia perfuming agents or odorants have left much to be desired as is clear for instance, from the aforementioned Guenther publication excerpts.

A particularly satisfactory procedure, which is both simple and inexpensive, for producing a 2-n-pentyl-3-(2-oxopropyl)-1-cyclopentanone which is free of a garlicky odor and which is effective for use in the practice of the present invention, comprises hydrolyzing and decarboxylating a compound of the formula

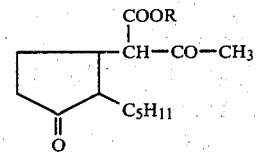

wherein R represents a hydrocarbyl group, particularly an alkyl group, and especially a lower alkyl group having from 1 to 5 carbon atoms, for instance, methyl or ethyl, with water, under pressure and in an initially substantially neutral medium. This hydrolysis and decarboxylation under substantially neutral conditions produces the 2-n-pentyl-3-(2-oxopropyl)-1-cyclopentanone free from any garlicky or other objectionable odors; and in a good yield; and it avoids the formation of products derived by an intramolecular condensation reaction which occurs when the hydrolysis is effected in an acid or an alkaline medium. Processes for such production of 2-n-pentyl-3-(2-oxopropyl)-1-cyclopentanone are described below, the aforesaid starting compound I being initially prepared by condensing 2-n-pentyl-cyclopent-2-en-1-one with a keto-ester of the formula

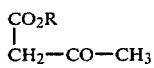

$$\begin{array}{c} CO_2R \\ | \\ CH_2-CO-CH_3 \end{array} \qquad II$$

where R represents a hydrocarbyl group as set forth above in regard to the starting compound of formula I.

The temperature at which the hydrolysis and decarboxylation is effected is variable and, generally speaking, simply affects the speed of the reaction. Conveniently, the hydrolysis and decarboxylation is carried out at a temperature of from 120° to 300° C., preferably from 140° to 260° C. The proportion of water used is also variable for carrying out the reaction but, conveniently, the reaction is effected using the same or substantially the same weight of water as of the starting compound of formula I. The reaction is normally effected in an autoclave from which the air is first purged.

The following Examples 1 and 2 are illustrative of especially satisfactory procedures for producing a 2-n-pentyl-3-(2-oxopropyl)-1-cyclopentanone which is free from a garlicky odor, and which possesses a magnolia odor, and which is useful in the production of the perfumed compositions of the present invention.

EXAMPLE 1

(a) One liter of absolute ethanol was introduced into a 4 liter flask. Then 23 g of sodium were added to it, and 650 g of ethyl acetoacetate were then added to the resulting sodium ethylate solution, after which 456 g of 2-n-pentyl-cyclopent-2-en-1-one were added dropwise over 1 hour. The solution thus obtained was heated over a period of 2 hours up to the reflux temperature (87° C.), held at this temperature for 3 hours, then allowed to cool and stand at ambient temperature for 16 hours. The resulting product was neutralised with 65 g of acetic acid and subsequently poured onto 3,300 ml of a 10% aqueous sodium chloride solution. The aqueous layer was then decanted off and extracted 3 times with the aid of 300 ml of toluene. The toluene extracts were washed to neutrality, the toluene was removed by distillation and the remainder fractionally distillated. There was thus obtained 513 g of 2-n-pentyl-3-(1-carbethoxy-2-oxopropyl)-1-cyclopentanone. Yield=60%.

(b) 513 g of 2-n-pentyl-3-(1-carbethoxy-2-oxopropyl)-1-cyclopentanone were mixed in an autoclave with an equal weight of water. The autoclave was then purged of the air which it contained, closed and heated up to a temperature of 140°–150° C. for 2 hours. After cooling, extraction, washing and distillation, there was obtained 332 g of 2-n-pentyl-3-(2-oxopropyl)-1-cyclopentanone (yield=90.6%) having $n_D^{20}=1.432$ and $d_4^{20}=0.961$.

EXAMPLE 2

(a) 750 ml of absolute methanol was introduced into a 2 liter flask. Then 17.3 g of sodium were added thereto, and 580 g of methyl acetoacetate were then added after which 456 g of 2-n-pentyl-cyclopent-2-en-1-one were added and the mixture was allowed to stand for 48 hours at the ambient temperature. The reaction product was neutralised with 45 g of acetic acid and then poured into 3 liters of a 10% aqueous sodium chloride solution. The product was then worked up as described in Example 1 (a). There were thus obtained 567 g (yield=70%) of 2-n-pentyl-(1-carbomethoxy-2-oxopropyl)-1-cyclopentanone having: $n_D^{20}=1.4702$, $d_4^{20}=1.0545$.

(b) 567 g of 2-n-pentyl-(1-carbomethoxy-2-oxopropyl)-1-cyclopentanone were mixed with an equal weight of water and heated according to the process described in Example 1 (b). There were obtained 391 g of 2-n-pentyl-3-(2-oxopropyl)-1-cyclopentanone (overall yield=80% based on the amount of 2-n-pentyl-cyclopent-2-en-1-one consumed) having the physical constants shown in Example 1 (b).

Illustrative perfumed compositions made in accordance with the present invention are set forth below in Examples 3 and 4 in the form of perfumes. As previously indicated, in accordance with the present invention, not only can perfumes be prepared by the utilization of the garlicky free 2-n-pentyl-3-(2-oxopropyl)-1-cyclopentanone but also perfumed products illustrative of which are, for example, solid and liquid detergents, synthetic washing agents, aerosols and cosmetic products of all kinds. The following are examples of perfumes.

EXAMPLE 3

| Perfume | |
|---|---|
| Bergamotte peel Oil Extra | 60 |
| Benzyl acetate | 140 |
| Phenylethyl alcohol | 150 |
| Jasmin Absolute | 50 |
| Linalol | 50 |
| Methylnonylacetaldehyde C.12, 10% in ethylphthalate (E.P.) | 60 |
| C.11 aldehyde 10% in E.P. | 20 |
| Hydroxydihydrocitronellal | 140 |
| α-Ionone | 20 |
| Geranium Oil Africa | 60 |
| Civet Absolute 10% in E.P. | 10 |
| Hyacinth Absolute | 10 |
| Vetiver Oil Bourbon | 35 |
| Cyclopentadecanolide | 20 |
| Tonka beans absolute | 20 |
| Rose Oil Eastern | 15 |
| Musk ketone | 30 |
| α-Amylcinnamaldehyde | 30 |
| 2-pentyl-3-(2-oxo-propyl)-1-cyclopentanone | 80 |
| | 1,000 |

EXAMPLE 4

| Perfume | |
|---|---|
| Bergamotte Oil | 100 |
| Lemon Oil | 40 |
| Lavender Oil | 50 |
| Galbanum Oil 10% in E.P. | 100 |
| Patchouli Oil | 30 |
| Ylang-Ylang Extra | 50 |
| Hydroxydihydrocitronellal | 150 |
| Rose Absolute, Centifolia | 20 |
| Jasmin Absolute | 40 |
| C.11 aldehyde 10% in E.P. | 10 |
| C.12 aldehyde 10% in E.P. | 20 |
| Trimethylundecanal 10% in E.P. | 10 |
| Phenylethyl alcohol | 50 |
| Geraniol | 60 |

-continued

| Perfume | |
|---|---|
| Guaiol acetate | 40 |
| Oak moss absolute | 10 |
| Kephalis | 40 |
| Cyclohexadecanolide | 20 |
| Musk ketone | 30 |
| Coumarin | 30 |
| 2-n-pentyl-3-(2-oxo-propyl)-1-cylopentanone | 100 |
| | 1,000 |

The term "perfumes" is used herein and in the claims to mean a mixture of a plurality of odorant organic compounds which are blended together in various proportions so that said mixture of odorant compounds produces a pleasant fragrance, with or without, but commonly with, organic solvents or mixtures of organic solvents in which said odorants are soluble, such organic solvents usually falling into the category of esters, ketones, aldehydes or hydrocarbons or mixtures of such organic solvents.

As illustrative of the effect of the 2-n-pentyl-3-(2-oxo-propyl)-1-cyclopentanone free from garlicky odor in the perfume compositions of the above Examples 3 and 4, comparisons were made with otherwise the same perfume compositions but minus said 2-n-pentyl-3-(2-oxo-propyl)-1-cyclopentanone.

The perfume of Example 3 minus the 2-n-pentyl-3-(2-oxo-propyl)-1-cyclopentanone had the quite classical floral aldehydic, woody and musk-like aspect of a typical perfume, favored in former years, having a floral-rose-like odor with an essentially jasmin-like odor and warm and animal notes which were fixed by the civet absolute and the tonka bean absolute, and it qualified as a classical pattern of a quality perfume.

The inclusion of the 2-n-pentyl-3-(2-oxo-propyl)-1-cyclopentanone, whereby to produce the perfume of Example 3, resulted in a substantial change and improvement, the perfume, as a result of said inclusion, acquiring a new floral component which perfumers had not previously been able to obtain, which new floral component is that of a magnolia odor. In addition, the effects of the blends of the hydroxycitronellal the musk and vetiver became enhanced in being more alive and vibrant, and the perfume took on a substantially greater power and character.

In the case of the perfume of Example 4, but minus the 2-n-propyl-3-(2-oxo-propyl)-1-cyclopentanone, said perfume was also of classical character but olfactively very different from that of Example 3 minus the 2-n-propyl-3-(2-oxo-propyl)-1-cyclopentanone. The floral heart of said perfume of Example 4 minus the 2-n-pentyl-3-(2-oxo-propyl)-1-cyclopentanone was jasmin-like and rose-like. The addition of the 2-n-pentyl-3-(2-oxo-propyl)-1-cyclopentanone, whereby to produce the perfume of Example 4, resulted in a perfume which was no longer just jasmin-like and rose-like with all of the nuances associated therewith but, rather, it became enriched and refreshed and took on a distinct inflexion of magnolia flowers with enhancement of the muguet-wood-musk-like aspects with respect to the matter of lasting effects. The foregoing test comparisons were made by the well accepted paper absorption smelling technique as conventionally carried out by expert perfumers for evaluating and comparimg perfumes.

It will be seen, from the foregoing description of the present invention and the illustrative Examples 3 and 4 perfumed compositions, that the perfumed compositions may take various forms so far as their compositional character is concerned, always provided, of course, that they contain a carrier, particularly such as those given by way of illustration, and that they contain up to 20% preferably from 1 to about 20%, by weight, of the perfumed compositions, of the compound 2-n-pentyl-3-(2-oxopropyl)-1-cyclopentanone free from a garlicky odor and possessing a magnolia odor. Perfumes for example, made according to the invention may contain, in conjunction with the said 2-n-pentyl-3-(2-oxo-propyl)-1-cyclopentanone, non-magnolia floral odorants, such as a plurality of floral odorants of non-alkyl cyclopentenone structure; or a plurality of floral odorants at least most of which are organic compounds of non-alkyl cyclopentenone structure; and such perfumes may also contain jasmin as one of the odorant constituents thereof.

I claim:

1. Perfumed compositions having a magnolia odor, said compositions containing a carrier and, in addition, as an odorant compound 2-n-pentyl-3-(2-oxo-propyl)-1-cyclopentanone having a magnolia odor and free from a garlicky odor and effective to impart a magnolia odor to said compositions, said compound being present in an effective amount of and up to about 20%, by weight, of the compositions.

2. Perfumed compositions having a magnolia odor, said compositions containing a carrier and, in addition, as an odorant compound 2-n-pentyl-3-(2-oxo-propyl)-1-cyclopentanone having a magnolia odor and free from a garlicky odor and effective to impart a magnolia odor to said compositions, said compound being present in proportions in the range of about 1 to about 20%, by weight, of the compositions.

3. Perfumed compositions according to claim 1, in which said compositions are perfumes.

4. A composition according to claim 3, in which said perfumes contain non-magnolia floral odorants, and in which said 2-n-pentyl-3-(2-oxo-propyl)-1-cyclopentanone free of garlicky odors serves to fix and magnify said non-magnolia floral odorants.

5. Perfumed compositions according to claim 3, in which said perfumes contain a plurality of odorants of non-alkyl cyclopentanone structure.

6. Perfumed compositions according to claim 5, in which said perfumes also include jasmin as one of said odorants.

7. Perfumed compositions containing a carrier and, in addition, a plurality of floral odorants at least most of which are organic compounds of non-alkyl cyclopentanone structure, and an effective amount of and up to about 20%, by weight of said compositions, of the compound 2-n-pentyl-3-(2-oxo-propyl)-1-cyclopentanone having a magnolia odor and free from a garlicky odor, said 2-n-pentyl-3-(2-oxo-propyl)-1-cyclopentanone serving as a fixative for at least some of said first-mentioned floral odorants.

8. Perfumed compositions according to claim 1, in which said odorant compound 2-n-pentyl-3-(2-oxopropyl)-1-cyclopentanone has a $n_D^{20}$=about 1.432 and $d_4^{20}$=about 0.961.

9. A composition according to claim 4, in which said odorant compound 2-n-pentyl-3-(2-oxopropyl)-1-cyclopentanone has a $n_D^{20}$=about 1.432 and $d_4^{20}$=about 0.961.

* * * * *